United States Patent
Rice

(10) Patent No.: US 7,638,676 B2
(45) Date of Patent: Dec. 29, 2009

(54) PROCESSES FOR THE ISOMERIZATION OF FEEDSTOCKS COMPRISING PARAFFINS OF 5 TO 7 CARBON ATOMS

(75) Inventor: Lynn H. Rice, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 257 days.

(21) Appl. No.: 11/851,576

(22) Filed: Sep. 7, 2007

(65) Prior Publication Data

US 2009/0069618 A1  Mar. 12, 2009

(51) Int. Cl.
*C07C 5/27* (2006.01)
*C07C 7/144* (2006.01)

(52) U.S. Cl. ...................................... 585/738; 585/818

(58) Field of Classification Search ................. 585/738, 585/818
See application file for complete search history.

(56) References Cited

U.S. PATENT DOCUMENTS

| | | | |
|---|---|---|---|
| 4,717,784 A | 1/1988 | Stem et al. ................... | 585/738 |
| 4,735,193 A | 4/1988 | Kulprathipanja et al. ... | 127/46.3 |
| 4,740,219 A | 4/1988 | Kulprathipanja et al. ........ | 55/16 |
| 4,804,802 A | 2/1989 | Evans et al. .................. | 585/734 |
| 4,804,803 A | 2/1989 | Schmidt et al. ............. | 585/748 |
| 4,925,459 A | 5/1990 | Rojey et al. .................... | 155/16 |
| 4,925,562 A | 5/1990 | Te Hennepe et al. ... | 210/500.25 |
| 5,036,035 A | 7/1991 | Baba et al. ................... | 502/221 |
| 5,069,794 A | 12/1991 | Haag et al. ................... | 210/650 |
| 5,127,925 A | 7/1992 | Kulprathipanja et al. ........ | 55/16 |
| 5,146,037 A | 9/1992 | Zarchy et al. ............... | 585/738 |
| 5,326,296 A | 7/1994 | De Jesus ...................... | 441/60 |
| 5,705,730 A | 1/1998 | Zarchy et al. ............... | 585/738 |
| 5,922,639 A | 7/1999 | Alario et al. ................. | 502/230 |
| 5,968,366 A | 10/1999 | Deckman et al. ............ | 210/651 |
| 6,001,241 A | 12/1999 | Gosling et al. ................ | 208/65 |
| 6,013,173 A | 1/2000 | Bogdan ...................... | 208/139 |
| 6,036,845 A | 3/2000 | Funk et al. .................... | 208/65 |
| 6,090,289 A | 7/2000 | Verduijn et al. ............. | 210/644 |

(Continued)

FOREIGN PATENT DOCUMENTS

EP  0 666 109 A1  1/1995

(Continued)

OTHER PUBLICATIONS

Separation of Normal Paraffins from Isoparaffins presented by I. A. Reddock, et al, at the Eleventh Australian Conference on Chemical Engineering, Brisbane, Sep. 4-7, 1983.

(Continued)

*Primary Examiner*—Thuan Dinh Dang
(74) *Attorney, Agent, or Firm*—Maryann Maas

(57) ABSTRACT

In an isomerization process where the isomerization effluent (114) is fractionated in a deisohexanizer (116) to provide a lower boiling fraction (122) containing dimethylbutanes, a higher boiling fraction containing methylpentanes and a bottoms stream (120) containing normal hexane and heavies, the bottoms stream is contacted with a selective permeation membrane (124) to provide a normal hexane-containing permeate (128) suitable for recycle to the isomerization. The energy consumption of the deisohexanizer (116) can be reduced without adversely affecting the octane rating of the overhead (122).

7 Claims, 1 Drawing Sheet

U.S. PATENT DOCUMENTS

| | | | |
|---|---|---|---|
| 6,156,950 A | 12/2000 | Ragil et al. | 585/802 |
| 6,214,764 B1 | 4/2001 | Gillespie | 502/230 |
| 6,248,682 B1 | 6/2001 | Thompson et al. | 502/4 |
| 6,338,791 B1 | 1/2002 | Ragil et al. | 208/63 |
| 6,407,301 B1 | 6/2002 | Foley et al. | 585/650 |
| 6,503,295 B1 | 1/2003 | Koros et al. | 95/51 |
| 6,818,333 B2 | 11/2004 | Chau et al. | 428/702 |
| 6,818,589 B1 | 11/2004 | Gillespie | 502/326 |
| 2003/0196931 A1 | 10/2003 | Houzvicka et al. | 208/65 |
| 2005/0283037 A1 | 12/2005 | Briot et al. | 585/535 |

FOREIGN PATENT DOCUMENTS

| | | |
|---|---|---|
| WO | WO 2005/012397 A2 | 2/2005 |
| WO | WO 2005/049766 A1 | 6/2005 |

OTHER PUBLICATIONS

McKeown, et al., Chem. Commun., 2780 (2002).
McKeown, et al.,, Chem. Eur. J., 11:2610 (2005).
Budd, et al., J. Mater. Chem., 13:2721 (2003).
Budd, et al., Adv. Mater., 16:456 (2004).
Budd, et al., Chem Commun., 230 (2004).

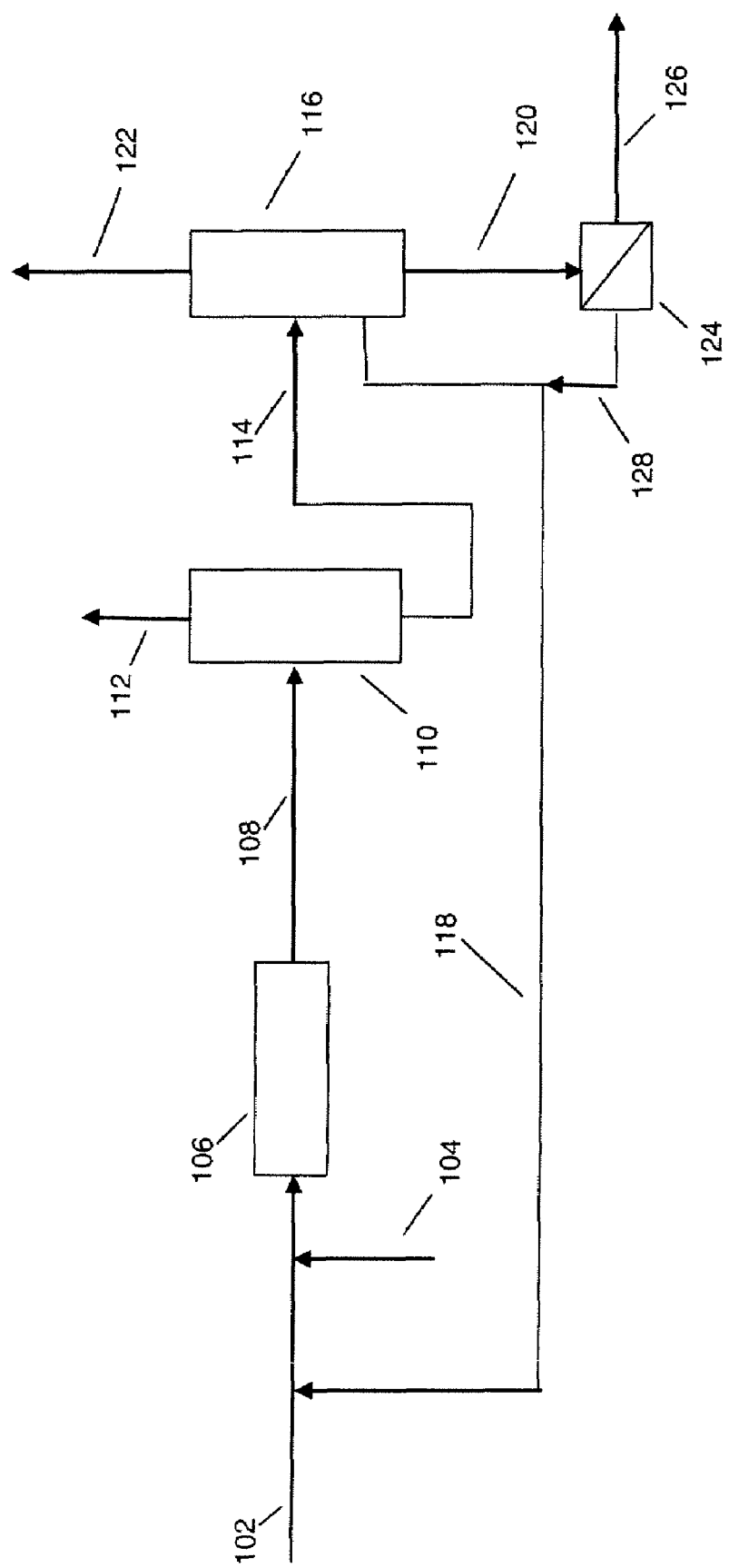

PROCESSES FOR THE ISOMERIZATION OF FEEDSTOCKS COMPRISING PARAFFINS OF 5 TO 7 CARBON ATOMS

BACKGROUND OF THE INVENTION

This invention relates to improved processes for the isomerization of paraffins of 5 to 7 carbon atoms, e.g., to provide isomerate having enhanced Research Octane Number for blending into gasoline pools, and particularly to such processes using a deisohexanizer.

Processes for the isomerization of paraffins into more highly branched paraffins are widely practiced. Particularly important commercial isomerization processes are used to increase the branching, and thus the octane value of refinery streams containing paraffins of 4 to 8, especially 5 to 7, carbon atoms. The isomerate is typically blended with a refinery reformer effluent to provide a blended gasoline mixture having a desired research octane number (RON).

The isomerization process proceeds toward a thermodynamic equilibrium. Hence, the isomerate will still contain normal paraffins that have low octane ratings and thus detract from the octane rating of the isomerate. Provided that adequate high octane blending streams such as alkylate and reformer effluent is available and that gasolines of lower octane ratings, such as 85 and 87 RON, are in demand, the presence of these normal paraffins in the isomerate has been tolerated.

Where circumstances demand higher RON isomerates, the isomerization processes have been modified by separating the normal paraffins from the isomerate and recycling them to the isomerization reactor. Thus, not only are normal paraffins that detract from the octane rating removed from the isomerate but also their return to the isomerization reactor increases the portion of the feed converted to the more highly desired branched paraffins.

The major processes for the separation of the normal paraffins from the isomerate are the use of adsorptive separation such as disclosed in U.S. Pat. Nos. 4,717,784 and 4,804,802, and distillation. The most frequently practiced isomerization processes that recycle normal paraffins use a deisohexanizer. A deisohexanizer is one or more distillation columns where an overhead containing branched $C_6$ paraffins such as dimethylbutanes (2,2-dimethylbuthane and 2,3-dimethylbutane) and lighter components is obtained as the isomerate product for, e.g., blending for gasolines, and a side-stream containing normal hexane and similarly boiling components such as methylpentanes (2-methylpentane and 3-methylpentane) and methylcyclopentane is recycled to the isomerization reactor. Often, the RON (research octane number) rating of the overhead from a deisohexanizer is in the range of 86 to 88.

One of the problems with a deisohexanizer is that high reflux ratios, and thus substantial reboiler duty, are required to effect separation of closely boiling compounds having substantially differing octane values such as methyl pentanes and dimethylbutanes. Similarly, the deisohexanizer is required to effect a separation among hydrocarbons such as normal hexane, which is sought for isomerization to high octane isomers and heavies containing 7 and more carbons. Often, the heat duty for a deisohexanizer may be in the range of 15 or more kilocalories per liter of feed.

Separation of linear from branched paraffins has also been proposed, but membranes have yet to find a practical, commercial application. U.S. Pat. No. 5,069,794 discloses microporous membranes containing crystalline molecular sieve material. At column 8, lines 11 et seq., potential applications of the membranes are disclosed including the separation of linear and branched paraffins. See also, U.S. Pat. No. 6,090,289, disclosing a layered composite containing molecular sieve that could be used as a membrane. Among the potential separations in which the membrane may be used that are disclosed commencing at column 13, line 6, include the separation of normal paraffins from branched paraffins. U.S. Pat. Nos. 6,156,950 and 6,338,791 discuss permeation separation techniques that may have application for the separation of normal paraffins from branched paraffins and describe certain separation schemes in connection with isomerization. US Publication 2003/0196931 discloses a two-stage isomerization process for up-grading hydrocarbon feeds of 4 to 12 carbon atoms.

Recently, Bourney, et al., in WO 2005/049766 disclose a process for producing high octane gasoline using a membrane to remove, inter alia, n-pentane from an isomerized stream derived from the overhead of a deisohexanizer. A side cut from the deisohexanizer is as a sweep fluid on the permeate side of the membrane. The mixture of the permeate and sweep fluid is recycled to the isomerization reactor. In a computer simulation based upon the use of an MFI on alumina membrane, example 1 of the publication indicates that 5000 square meters of membrane surface area is required to remove 95 mass percent of n-pentane from the overhead from a deisohexanizer distillation column. At the flow rate of feed to the permeator (75000 kg/hr. having 20.6 mass percent n-pentane), the flux of n-pentane used in the simulation appears to be in the order of 0.01 gram moles/$m^2$·s at 300° C. The RON of the product with the n-pentane removed is said to be 91.0.

The use of zeolite membranes is suggested as a suitable technique for separating linear molecules. See, for instance, paragraphs 0008 and 0032. U.S. Pat. No. 6,818,333 discloses thin zeolite membranes that are said to have a permeability of n-butane of at least $6 \cdot 10^{-7}$ mol/$m^2$·s·Pa and a selectivity of at least 250 of n-butane to isobutane.

Especially in a refinery where large volumes of hydrocarbon feeds are subjected to isomerization, extremely large membrane surface areas would have to be provided in order to achieve the sought separation of the linear paraffins. For instance, ZSM-5/Silicalite (MFI) membranes (a sieving membrane) available from NGK Insulators, Ltd., Japan, that have selectivity for the permeation of linear paraffins over branched paraffins, have a flux under operating conditions in the range of 0.1 to 1.0 milligram moles per second per square meter at a pressure differential of 15 to 500 kPa. Thus, the costs for commercially implementing such a membrane separation system using these membranes or the membranes of the type disclosed in U.S. Pat. No. 6,818,333 render it not competitive with respect to an adsorption separation system or a distillation separation such as a deisohexanizer.

Changes in environmental and fuel efficiency regulations can have a profound effect on the demand for isomerate of higher octane-ratings. For instance, requirements to reduce benzene content of gasolines would necessitate increasing the octane rating of isomerate and "once-though" isomerization processes will be required to be retrofitted to a cyclic process with the separation and return of normal paraffins to the isomerization reactor. Even existing cyclic processes that use deisohexanizers may be required to provide isomerate of enhanced octane rating.

Accordingly, processes are sought to reduce the costs of operating a deisohexanizer without adversely affecting the octane rating of deisohexanizer overhead.

For the purposes of the following discussion of the invention, the following membrane properties are defined.

Microporous

Microporous and microporosity refer to pores having effective diameters of between 0.3 to 2 nanometers.

Mesoporous

Mesoporous and mesoporosity refer to pores having effective diameters of between 2 and 50 nanometers.

Macroporous

Macroporous and macroporosity refer to pores having effective diameters of greater than 50 nanometers.

Nanoparticle

Nanoparticles are particles having a major dimension up to 100 nanometers.

Molecular Sieves

Molecular sieves are materials having microporosity and may be amorphous, partially amorphous or crystalline and may be zeolitic, polymeric, metal, ceramic or carbon.

Sieving Membrane

Sieving membrane is a composite membrane containing a continuous or discontinuous selective separation medium containing molecular sieve barrier. A barrier is the structure that exists to selectively block fluid flow in the membrane. In a continuous sieving membrane, the molecular sieve itself forms a continuous layer that is sought to be defect-free. The continuous barrier may contain other materials such as would be the case with mixed matrix membranes. A discontinuous sieving membrane is a discontinuous assembly of molecular sieve barrier in which spaces, or voids, exist between particles or regions of molecular sieve. These spaces or voids may contain or be filled with other solid material. The particles or regions of molecular sieve are the barrier. The separation effected by sieving membranes may be on steric properties of the components to be separated. Other factors may also affect permeation. One is the sorptivity or lack thereof by a component and the material of the molecular sieve. Another is the interaction of components to be separated in the microporous structure of the molecular sieve. For instance, for some zeolitic molecular sieves, the presence of a molecule, say, n-hexane, in a pore, may hinder 2-methylpentane from entering that pore more than another n-hexane molecule. Hence, zeolites that would not appear to offer much selectivity for the separation of normal and branched paraffins solely from the standpoint of molecular size, may in practice provide greater selectivities of separation.

$C_6$ Permeate Flow Index

The permeability of a sieve membrane, i.e., the rate that a given component passes through a given thickness of the membrane, often varies with changes in conditions such as temperature and pressure, absolute and differential. Thus, for instance, a different permeation rate may be determined where the absolute pressure on the permeate side is 1000 kPa rather than that where that pressure is 5000 kPa, all other parameters, including pressure differential, being constant. Accordingly, a $C_6$ Permeate Flow Index is used herein for describing sieving membranes. The $C_6$ Permeate Flow Index for a given membrane is determined by measuring the rate (gram moles per second) at which a substantially pure normal hexane (preferably at least 95 mass-percent normal hexane) permeates the membrane at approximately 150° C. at a retentate side pressure of 1000 kPa absolute and a permeate-side pressure of 100 kPa absolute. The $C_6$ Permeate Flow Index reflects the permeation rate per square meter of retentate-side surface area but is not normalized to membrane thickness.

Hence, the $C_6$ Permeate Flow Index for a given membrane will be in the units of gram moles of normal hexane permeating per second per square meter of retentate-side membrane surface area.

$C_6$ Permeate Flow Ratio

The $C_6$ Permeate Flow Ratio for a given sieve membrane is the ratio of the $C_6$ Permeate Flow Index (n-hexane) to an i-$C_6$ Permeate Flow Index wherein the i-$C_6$ Permeate Flow Index is determined in the same manner as the $C_6$ Permeate Flow Index but using substantially pure dimethylbutanes (regardless of distribution between 2,2-dimethylbutane and 2,3-dimethylbutane) (preferably at least 95 mass-percent dimethylbutanes).

SUMMARY OF THE INVENTION

By this invention improvements are made to isomerization processes for upgrading the octane rating of paraffin feedstocks comprising 5 to 7 carbon atoms, which processes use deisohexanizers to separate and recycle normal paraffins to isomerization reactors. Advantageously, the processes can reduce the operating costs of a deisohexanizer without adversely affecting the octane rating of the overhead from the deisohexanizer. In accordance with the processes of this invention, the deisohexanizer is operated such that a significant portion of the normal hexane contained in the feed to the deisohexanizer is removed with the bottoms stream and is recovered from the bottoms stream through a membrane separation.

Normal hexane is a sought linear paraffin for recycle to the isomerization reactor for conversion to higher octane dimethylbutanes. As the processes of this invention provide for the recovery of normal hexane from the bottoms stream, the heat duty for the deisohexanizer can be substantially reduced, often by at least 10 percent. Additionally, as the volume of the bottoms stream from a deisohexanizer is generally less than 20 percent of the volume of the feed stream, much less membrane surface area is required than for a membrane separation of the isomerate. In preferred aspects of the processes of this invention, the research octane rating of the overhead stream from the deisohexanizer ($C_{4+}$ RONC) is at least 88, preferably at least 88.5.

The broad aspects of the processes of this invention comprise:

(a) isomerizing a feedstock containing linear paraffins including linear paraffins having 5 to 7 carbon atoms wherein at least 15 mass-percent of the feedstock is linear paraffin under isomerization conditions including the presence of isomerization catalyst to provide an isomerization effluent containing linear paraffins including normal hexane but in a concentration less than that in the feedstock, (b) distilling at least a portion, preferably at least 90 mass-percent and most preferably essentially all, of the isomerization effluent to provide a lower boiling fraction containing dimethylbutanes, a higher boiling stream side draw stream containing normal hexane and methylpentanes, and a bottoms stream containing normal hexane and heavies, wherein the side stream contains less than 75, preferably between 20 and 70, mass percent of the normal hexane subjected to distillation in this step b, and the bottoms stream contains at least 25, preferably 30 to 80, mass percent of the normal hexane subjected to distillation in this step b, and (c) contacting at least a portion, preferably at least 90 mass-percent and most preferably essentially all, of the bottoms stream from step b with a retentate-side of a selectively permeable membrane under conditions including sufficient membrane surface area and pressure differential across the membrane to provide a retentate fraction of the bottoms stream that has a reduced concentration of normal hexane, and to provide across the membrane at a permeate-side, a permeate fraction having an increased concentration of normal hexane, said permeate fraction containing at least 50, preferably at least 75, and most preferably at least 90, mass-percent of the normal hexane contained in the bottoms steam contacted with the membrane.

Preferably at least a portion, more preferably at least 90 mass percent, and most preferably essentially all, of the permeate fraction of step c is recycled to step a.

Preferably the membrane is a sieving membrane having a $C_6$ Permeate Flow Index of at least 0.01, more preferably at least 0.02, and a $C_6$ Permeate Flow Ratio of at least 1.25:1, more preferably at least 1.3:1, and often 1.35:1 to 5:1 or 6:1.

The invention also pertains to apparatus suitable for conducting the processes of this invention. In broad aspects, the apparatus for isomerization of a feedstock comprising paraffins having between 5 and 6 carbon atoms to provide a gasoline fraction comprises:

a. an isomerization reactor (106) being adapted to receive feedstock at an inlet and having an outlet, b. a dehexanizer (116) having an inlet in fluid communication with the outlet of isomerization reactor (106), a lower boiling outlet adapted to remove a lower boiling fraction via line (122), a higher boiling outlet to provide a side-cut fraction (118) and a bottoms outlet (120); and c. a membrane separator (124) having a feed side inlet in fluid communication with the bottoms outlet (120), a permeate side outlet in fluid communication with the higher boiling outlet (118) of the dehexanizer (116), and a feed side outlet (126).

DESCRIPTION OF THE FIGURE

FIG. 1 is a schematic representation of processes in accordance with this invention using a stabilizer column prior to a deisohexanizer.

DETAILED DESCRIPTION OF THE INVENTION

Isomerization

Any suitable paraffin-containing feedstock may be used in the processes of this invention. Naphtha feedstocks are the most often used as the feedstocks to isomerization processes. Naphtha feedstocks comprise paraffins, naphthenes, and aromatics, and may comprise small amounts of olefins, boiling within the gasoline range. Feedstocks which may be utilized include straight-run naphthas, natural gasoline, synthetic naphthas, thermal gasoline, catalytically cracked gasoline, partially reformed naphthas or raffinates from extraction of aromatics. The feedstock essentially is encompassed by the range of a full-range naphtha, or within the range of 0° to 230° C. Usually the feedstock is light naphtha having an initial boiling point of 10° to 65° C. and a final boiling point from 75° to 110° C.; preferably, the final boiling point is less than 95° C.

Naphtha feedstocks generally contain small amounts of sulfur compounds amounting to less than 10 mass parts per million (mppm) on an elemental basis. Preferably the naphtha feedstock has been prepared from a contaminated feedstock by a conventional pretreating step such as hydrotreating, hydrorefining or hydrodesulfurization to convert such contaminants as sulfurous, nitrogenous and oxygenated compounds to $H_2S$, $NH_3$ and $H_2O$, respectively, which can be separated from hydrocarbons by fractionation. This conversion preferably will employ a catalyst known to the art comprising an inorganic oxide support and metals selected from Groups VIB(IUPAC 6) and VIII(IUPAC 9-10) of the Periodic Table. Water can act to attenuate catalyst acidity by acting as a base, and sulfur temporarily deactivates the catalyst by platinum poisoning. Feedstock hydrotreating as described hereinabove usually reduces water-generating oxygenates and deactivating sulfur compounds to suitable levels, and other means such as adsorption systems for the removal of sulfur and water from hydrocarbon streams generally are not required. It is within the ambit of the present invention that this optional pretreating step be included in the present process combination.

The principal components of the preferred feedstock are cyclic and acyclic paraffins having from 4 to 7 carbon atoms per molecule ($C_4$ to $C_7$), especially $C_5$ to $C_6$, and smaller amounts of aromatic and olefinic hydrocarbons also may be present. Usually, the concentration of $C_7$ and heavier components is less than 20 mass-percent of the feedstock. Although there are no specific limits to the total content in the feedstock of cyclic hydrocarbons, the feedstock generally contains between 2 and 40 mass-percent of cyclics comprising naphthenes and aromatics. The aromatics contained in the naphtha feedstock, although generally amounting to less than the alkanes and cycloalkanes, may comprise from 2 to 20 mass-percent and more usually 5 to 10 mass-percent of the total. Benzene usually comprises the principal aromatics constituent of the preferred feedstock, optionally along with smaller amounts of toluene and higher-boiling aromatics within the boiling ranges described above.

In general, the feedstocks used in the processes of this invention comprise at least 15, often from 40, preferably at least 50, mass-percent to essentially all linear paraffins. For naphtha feedstocks, linear paraffins are typically present in amounts of at least to 50, say, 50 to 90, mass-percent. The mass ratio of non-linear paraffins to linear paraffins in the feedstocks is often less than 1:1, say, 0.1:1 to 0.95:1. Non-linear paraffins include branched acyclic paraffins and substituted or unsubstituted cycloparaffins. Other components such as aromatics and olefinic compounds may also be present in the feedstocks as described above.

The feedstock is passed to one or more isomerization zones. In the aspects of this invention where normal hexane is recycled, the feedstock and recycle are usually admixed prior to entry into the isomerization zone, but if desired, may be separately introduced. In any case, the total feed to the isomerization zone is referred to herein as the isomerization feed. The recycle may be provided in one or more streams. As discussed later, the recycle contains linear paraffins. The concentration of linear paraffins in the isomerization feed will not only depend upon the concentration of linear paraffins in the feedstock but also the concentration in the recycle and the relative amount of recycle to feedstock, which can fall within a wide range. Often, the isomerization feed has a linear paraffins concentration of at least 30, say, between 35 and 90, preferably 40 to 70, mass-percent, and a mole ratio of non-linear paraffins to linear paraffins of between 0.2:1 to 1.5:1, and sometimes between 0.4:1 to 1.2:1.

In the isomerization zone the isomerization feed is subjected to isomerization conditions including the presence of isomerization catalyst preferably in the presence of a limited but positive amount of hydrogen as described in U.S. Pat. Nos. 4,804,803 and 5,326,296, both herein incorporated by reference. The isomerization of paraffins is generally considered a reversible first order reaction. Thus, the isomerization reaction effluent will contain a greater concentration of non-linear paraffins and a lesser concentration of linear paraffins than does the isomerization feed. In preferred embodiments of this invention, the isomerization conditions are sufficient to isomerize at least 20, preferably, between 30 and 60, mass-percent of the normal paraffins in the isomerization feed. In general, the isomerization conditions achieve at least 70, preferably at least 75, say, 75 to 97, percent of equilibrium for $C_6$ paraffins present in the isomerization feed. In many instances, the isomerization reaction effluent has a mass ratio of non-linear paraffins to linear paraffins of at least 2:1, preferably between 2.5 to 4:1.

The isomerization catalyst is not critical to the broad aspects of the processes of this invention, and any suitable isomerization catalyst may find application. Suitable isomerization catalysts include acidic catalysts using chloride for maintaining the sought acidity and sulfated catalysts. The isomerization catalyst may be amorphous, e.g. based upon amorphous alumina, or zeolitic. A zeolitic catalyst would still normally contain an amorphous binder. The catalyst may comprise a sulfated zirconia and platinum as described in U.S. Pat. No. 5,036,035 and European application 0 666 109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. These documents are incorporated herein for their teaching as to catalyst compositions, isomerization operating conditions and techniques.

Contacting within the isomerization zones may be effected using the catalyst in a fixed-bed system, a moving-bed system, a fluidized-bed system, or in a batch-type operation. A fixed-bed system is preferred. The reactants may be contacted with the bed of catalyst particles in upward, downward, or radial-flow fashion. The reactants may be in the liquid phase, a mixed liquid-vapor phase, or a vapor phase when contacted with the catalyst particles, with excellent results being obtained by application of the present invention to a primarily liquid-phase operation. The isomerization zone may be in a single reactor or in two or more separate reactors with suitable means therebetween to insure that the desired isomerization temperature is maintained at the entrance to each zone. Two or more reactors in sequence are preferred to enable improved isomerization through control of individual reactor temperatures and for partial catalyst replacement without a process shutdown.

Isomerization conditions in the isomerization zone include reactor temperatures usually ranging from 40° to 250° C. Lower reaction temperatures are generally preferred in order to favor equilibrium mixtures having the highest concentration of high-octane highly branched isoalkanes and to minimize cracking of the feed to lighter hydrocarbons. Temperatures in the range of from 100° to 200° C. are preferred in the present invention. Reactor operating pressures generally range from 100 kPa to 10 MPa absolute, preferably between 0.5 and 4 MPa absolute. Liquid hourly space velocities range from 0.2 to 25 volumes of isomerizable hydrocarbon feed per hour per volume of catalyst, with a range of 0.5 to 15 $hr^{-1}$ being preferred.

Hydrogen is admixed with or remains with the isomerization feed to the isomerization zone to provide a mole ratio of hydrogen to hydrocarbon feed of from 0.01 to 20, preferably from 0.05 to 5. The hydrogen may be supplied totally from outside the process or supplemented by hydrogen recycled to the feed after separation from isomerization reactor effluent. Light hydrocarbons and small amounts of inerts such as nitrogen and argon may be present in the hydrogen. Water should be removed from hydrogen supplied from outside the process, preferably by an adsorption system as is known in the art. In a preferred embodiment the hydrogen to hydrocarbon mol ratio in the reactor effluent is equal to or less than 0.05, generally obviating the need to recycle hydrogen from the reactor effluent to the feed.

Especially where a chlorided catalyst is used for isomerization, the isomerization reaction effluent is contacted with a sorbent to remove any chloride components such as disclosed in U.S. Pat. No. 5,705,730.

Deisohexanizer and Membrane Separation

The isomerization reaction effluent is subjected to one or more separation operations to provide a product fraction of an enhanced octane rating and, optionally, to remove other components such as hydrogen, lower alkanes and, especially with respect to chlorided catalysts, halogen compounds.

In a commonly practiced isomerization process, the isomerization is conducted in the liquid phase and the isomerization reaction effluent is passed to a product separator in which a gaseous overhead containing hydrogen and lower alkane is obtained. At least a portion of this hydrogen can be recycled to the isomerization reactor for providing at least a portion of the sought hydrogen for the isomerization. The liquid bottoms is passed to a distillation assembly (deisohexanizer) to provide a lower boiling fraction containing dimethylbutanes and a higher boiling normal hexane-containing fraction. Most often, the deisohexanizer is adapted to provide the normal hexane-containing stream as a side stream and provides a bottoms stream comprising normal heptane. The deisohexanizer may be a packed or trayed column and typically operates with a top pressure of between 50 and 500 kPa (gauge) and a bottoms temperature of between 750 and 170° C.

The composition of the lower boiling fraction from the deisohexanizer will depend upon the operation and design of the assembly and any separation processes to which the isomerization effluent has been subjected. For instance, if the stream to the deisohexanizer contains lights such as $C_1$ to $C_4$ compounds, the deisohexanizer may be adapted to provide an overhead fraction containing these lights, and a side-draw fraction containing $C_5$ compounds and branched $C_6$ compounds, especially dimethylbutanes. Typically the lower boiling fraction contains 20 to 60 mass-percent dimethylbutanes; 10 to 40 mass-percent normal pentane and 20 to 60 mass-percent isopentane and butane. Depending upon the operation of the deisohexanizer, the lower boiling fraction may also contain significant, e.g., at least 10 mass-percent methylpentanes.

The deisohexanizer is designed to provide a higher boiling fraction that contains methylpentanes, methylcyclopentane, a portion of the normal hexane, and cyclohexane, and a bottoms stream that contains normal hexane, cyclohexane and $C_7+$ hydrocarbons. At least a portion of the higher boiling fraction is recycled. As stated earlier, the distillation can be operated more economically by using lower reflux ratios and thus have more of the normal hexane pass into the bottoms stream. The reflux ratio used will depend upon the nature of the feed to the column as well as the design of the column and thus can vary over a broad range, e.g., from 1.5:1 to 2.5:1 on a mass basis of reflux to feed.

At least a portion, preferably at least 50, and more preferably at least 80, mass-percent to substantially all of the deisohexanizer bottoms stream is contacted with the retentate side of a selective membrane to provide a retentate that has a reduced concentration of normal hexane, and to provide across the membrane at a permeate-side, a permeate fraction containing normal hexane. Preferably the permeate fraction contains at least 75 mass-percent of the normal hexane contacted with the membrane. The permeate fraction often comprises at least 50, and sometimes between 60 and 95, mass percent normal hexane.

A pressure drop is maintained across the membrane in order to effect the desired separation at suitable permeation rates. The membrane may be of any suitable type including diffusion and sieving, and may be constructed of inorganic, organic or composite materials. For diffusion membranes, the driving force is the differential in partial pressures between the retentate and the permeate sides. In sieving membranes, the absolute pressure drop becomes a significant component of the driving force independent of partial pressures or concentrations. The preferred membranes are sieving membranes having a $C_6$ Permeate Flow Index of at least 0.01 and a $C_6$ Permeate Flow Ratio of at least 1.25:1. The sieving membranes are discussed in more detail below.

In the membrane separations, the pressure drop is often in the range of 0.1 to 10, preferably 0.2 to 2, MPa. In practice, the deisohexanizer overhead will be contacted with the retentate side of the membranes without additional compression to minimize capital and operating costs. The temperature for the membrane separation will depend in part on the nature of the membrane and on the temperature of the deisohexanizer overhead. Thus, for polymer-containing membranes, temperatures should be sufficiently low that the strength of the membrane is not unduly adversely affected. In most instances, the temperature for the separation is the temperature of the deisohexanizer overhead. Often the temperature is in the range of 25° C. to 150° C. Thus, the conditions of the membrane separation may provide for a liquid or gas or mixed phase on the retentate side of the membrane. Regardless of the phase of the fluid on the retentate side, the permeate may be a gas. If the fluid on the retentate side of the membrane is in the liquid phase, the permeate may be liquid, gaseous or mixed phase.

Any suitable selectively permeable membrane may be used in the apparatus and processes of this invention. The preferred membranes are sieving membranes. The membranes used in the processes of this invention are characterized in having high flux, i.e., having a $C_6$ Permeate Flow Index of at least 0.01. The membranes may be in any suitable form such as hollow fibers, sheets, and the like which can be assembled in a separator unit such as bundled hollow fibers or flat plate or spiral wound sheet membranes. The physical design of the membranes should enable, when assembled in the separator unit, sufficient pressure drop across the membrane to provide desirable flux. For hollow fiber membranes, the high pressure side (retentate side) is usually at the outside of the hollow fiber. The flow of the permeate may be co-current, countercurrent or cross-current with respect to the flow of the fluid on the retentate side of the membrane.

Preferably at least a portion of the normal hexane-containing permeate is recycled to the isomerization step.

Sieving Membranes

The preferred sieving membranes may be of various types, for instance, molecular sieves, pore-containing ceramic, metal, polymeric or carbon membranes, or composite membranes having a highly porous polymeric, metallic, molecular sieve, ceramic or carbon support with a thin sieving layer or barrier (molecular sieve), e.g., zeolitic, polymeric, metal, ceramic or carbon, having microporosity.

The membranes may be continuous or discontinuous. A discontinuous membrane comprises an assembly of small particle size microporous barrier whereas a continuous membrane comprises a continuous layer of microporous barrier. The membranes may be formed of a single material or they may be composites containing microporous barrier and support and, optionally, other structure. When making a thin, continuous barrier layer, as the thickness of the sieving layer decreases, the difficulties in obtaining a defect-free layer increase. As the processes of this invention do not require high selectivity, the membranes can contain minor defects. Typically continuous membranes are made by depositing or growing on a meso/macroporous structure, a continuous, thin layer of microporous barrier. Discontinuous assemblies of nano-sized microporous barrier enable very small permeating thicknesses to be achieved, but with the potential of by-pass. Discontinuous membranes use a meso/macroporous structure with which the microporous barrier is associated.

Examples of zeolite barrier include small pore molecular sieves such as SAPO-34, DDR, AlPO-14, AlPO-17, AlPO-18, AlPO-34, SSZ-62, SSZ-13, zeolite 3A, zeolite 4A, zeolite 5A, zeolite KFI, H-ZK-5, LTA, UZM-9, UZM-13, ERS-12, CDS-1, Phillipsite, MCM-65, and MCM-47; medium pore molecular sieves such as silicalite, SAPO-31, MFI, BEA, and MEL; large pore molecular sieves such as FAU, OFF, NaX, NaY, CaY, 13X, and zeolite L; and mesoporous molecular sieves such as MCM-41 and SBA-15. A number of types of molecular sieves are available in colloidal (nano-sized particle) form such as A, X, L, OFF, MFI, and SAPO-34. The zeolites may or may not be metal exchanged.

Other types of sieving materials include carbon sieves; polymers such as PIMs (polymers of intrinsic microporosity) such as disclosed by McKeown, et al., Chem. Commun., 2780 (2002); McKeown, et al., Chem. Eur. J., 11:2610 (2005); Budd, et al., J. Mater. Chem., 13:2721 (2003); Budd, et al., Adv. Mater., 16:456 (2004) and Budd, et al., Chem. Commun., 230 (2004); polymers in which porosity is induced by pore-forming agents such as poly(alkylene oxide), polyvinylpyrrolidone; cyclic organic hosts such as cyclodextrins, calixarenes, crown ethers, and spherands; microporous metal-organic frameworks such as MOF-5 (or IRMOF-1); glass, ceramic and metal shapes into which microporosity has been introduced.

In composite membranes, a meso/macroporous structure is used. The to meso/macroporous structure serves one or more functions depending upon the type membrane. It can be the support for the membrane composite, it can be an integral part of forming the microporous barrier, it can be the structure upon which or in which the microporous barrier is located. The meso/macroporous structure can be continuous or discontinuous, and the meso/macroporosity may thus be channels through the material of the meso/macroporous structure or be formed between particles that form the meso/macroporous structure. Examples of the latter are the AccuSep™ inorganic filtration membranes available from the Pall Corp. having a zirconia layer on a porous metal support wherein the zirconia is in the form of spherical crystals.

The meso/macroporous structure preferably defines channels, or pores, in the range of 2 to 500, preferably, 10 to 250, more preferably between 20 and 200, nanometers in diameter, and has a high flux. In more preferred embodiments, the $C_6$ Permeant Flow Index of the meso/macroporous structure is at least 1, and most preferably at least 10, and sometimes at least 1000. The meso/macroporous structure may be isotropic or anisotropic. The meso/macropores may be relatively straight or tortuous.

The meso/macroporous structure may be composed of inorganic, organic or mixed inorganic and organic material. The selection of the material will depend upon the conditions of the separation as well as the type of meso/macroporous structure formed. The material of the meso/macroporous structure may be the same or different than the material for the molecular sieve. Examples of porous structure compositions include metal, alumina such as alpha-alumina, gamma alumina and transition aluminas, molecular sieve, ceramics, glass, polymer, and carbon. In preferred embodiments, defects in the substrate are repaired prior to providing the barrier or precursor to the barrier. In another embodiment, the substrate may be treated with a silica sol to partially occlude pores and facilitate deposition of the barrier or precursor to the barrier. The silica particles will still provide sufficient space between their interstices to allow high flux rates. Another technique is to coat the support with silicon rubber or other polymer that permits high flux but occludes defects in the support or in the barrier.

If the meso/macroporous structure does not so serve, the membrane can contain a porous support for the meso/macroporous structure. The porous support is typically selected on the basis of strength, tolerance for the conditions of the intended separation and porosity.

The AccuSep™ inorganic filtration membranes available from Pall Corp. and similar types of meso/macroporous structures are particularly advantageous since the meso/macroporous structure can be thin thereby avoiding undue thicknesses of molecular sieve being grown. Further, the zirconia is relatively inert to zeolite-forming precursor solutions and synthesis and calcination conditions, making it a preferred meso/macroporous structure for these types of sieving membrane.

High flux is achieved through at least one of the following techniques: first, using a larger pore than required for normal alkane to pass; and second, using an extremely thin pore-containing layer. Where high flux is achieved using larger, less selective micropores in the microporous barrier, adequate separation may be achieved. Often the pores for these types of membranes have an average pore diameter of greater than 5.0 Å (average of length and width), say, 5.0 to 7.0 or 8 Å. Preferably, the structures have an aspect ratio (length to width) of less than 1.25:1, e.g., 1.2:1 to 1:1. For molecular sieve-containing membranes, exemplary structures are USY, ZSM-12, SSZ-35, SSZ-44, VPI-8, and Cancrinite. In some instances, a permeating molecule in a micropore may assist in enhancing selectivity. For instance, a normal hydrocarbon in a pore may decrease the rate at which a branched hydrocarbon can enter the pore as compared to another normal hydrocarbon.

High flux can also be achieved using very thin microporous barrier in either a continuous or discontinuous membrane. The microporous barrier can, if desired, be selected from sieving structures having micropores that are substantially impermeable to the moiety sought to be retained on the retentate side. In general, the pores for these types of membranes have an average pore diameter of up to 5.5 Å, for instance, 4.5 to 5.4 Å. The aspect ratio of the pores of these membranes may vary widely, and is usually in the range of 1.5:1 to 1:1. For molecular sieve-containing membranes, exemplary structures are ZSM-5, silicalite, ALPO-11, ALPO-31, ferrierite, ZSM-11, ZSM-57, ZSM-23, MCM-22, NU-87, UZM-9, and CaA.

Membranes comprising a discontinuous assembly of microporous barrier are characterized in that the barrier has a major dimension less than 100 nanometers, and the microporous barrier is associated with a meso/macroporous structure defining fluid flow pores, wherein barrier is positioned to hinder fluid flow through the pores of the meso/macroporous structure. A molecular sieve barrier is "associated" with a meso/macroporous structure when it is positioned on or in the structure whether or not bonded to the structure. Hence, nano-sized particles or islands of molecular sieve are used as barriers for the membranes. The discontinuous, microporous barrier is positioned to hinder fluid flow through fluid flow channels defined by the meso/macroporous structure. The barrier may be at least partially occluding the opening of a fluid flow channel of the meso/macroporous structure and/or within the fluid flow channel. Due to the small size of the particles or islands forming the discontinuous assembly of microporous barrier, some selectivity of separation is achievable despite the discontinuity.

Typically the size and configuration of the molecular sieve particles and the size and configuration of the meso/macropores in the meso/macroporous structure will be taken into account in selecting the components for the sieving membranes. With more spherical molecular sieve particles, such as silicalite, it is preferred to select a meso/macroporous structure having pores that are close to the same effective diameter. In this manner, the molecular sieve particles, if placed in, or partially in, the pores of the meso/macroporous structure, will provide minimal void space for by-pass. More flexibility exists with platelets and irregular shaped molecular sieve particles as they can overlap with little or no void space. In some instances a combination of molecular sieve configurations may be desirable. For instance, a spherical molecular sieve may be drawn into the pores of a meso/macroporous structure with smaller, more plate-like molecular sieve particles being subsequently introduced. The complementary functions are that the sphere serves as a support for the plate-like particles and the plate-like particles overlap to reduce by-pass. While the molecular sieves will likely be different compositions, and thus have different microporosity size and configuration, the benefit is enhanced separation without undue loss of permeance.

Where zeolitic molecular sieves are used, obtaining small particles is important to obtaining the high flux in a discontinuous microporous barrier. For many zeolites, seed particles are available that are less than 100 nanometers in major dimension. Most molecular sieves are made using organic templates that must be removed to provide access to the cages. Typically this removal is done by calcination. As discussed later, the calcination may be effected when the template-containing molecular sieves are positioned in a macropore such that undue agglomeration is avoided simply by limiting the number of particles that are proximate. Another technique for avoiding agglomeration of the zeolite particles during calcination is to silate the surface of the zeolite, e.g., with an aminoalkyltrialkoxysilane, aminoalkylalkyldialkoxysilane, or aminoalkyldialkylalkoxysilane. The amount of silation required will depend upon the size of the zeolite and its composition as well as the conditions to be used for calcination. In general, between 0.1 to 10 millimoles of silane are used per gram of zeolite.

Various techniques exist for providing the molecular sieve particles on or in the meso/macroporous support in a manner that at least partially occludes the meso- or macropores in the support. The specific technique to be used will depend upon the size and configuration of the molecular sieve particles, the size and configuration of the meso/macropores in the meso/macroporous structure, and the desired placement of the molecular sieve in or on the meso/microporous structure.

Especially where molecular sieve is placed on the surface of a meso/macroporous structure to occlude at least a portion of the opening of the pores, the meso/macroporous structure may be wet with a solution, or suspension, of nano-sized molecular sieve. The concentration of molecular sieve in the suspension should be sufficiently low that upon drying, the resulting layer of molecular sieve is not unduly thick. Advantageously at least a slight pressure drop is maintained across the meso/macroporous structure during the coating such that a driving force will exist to draw molecular sieve to any pores in the meso/macroporous structure that have not been occluded. Usually the suspension will be an aqueous suspension, although suspensions in alcohols and other relatively inert liquids can be used advantageously, at a concentration of between 2 and 30, say 5 and 20, mass percent. Where a pressure differential is used, the pressure differential is generally in the range of 10 to 200 kPa. One or more coats of molecular sieve may be used, preferably with drying between coats. Drying is usually at an elevated temperature, e.g., between 30° C. and 150° C., for 1 to 50 hours. Vacuum may be used to assist drying. Where zeolites are used as the molecular sieve, calcining, e.g., at a temperature of between 450° C. and 600° C. may, in some instances, assist in securing the molecular sieve to the meso/macroporous structure. Calcining may also serve to agglomerate the molecular sieve particles and thus reduce voids and the size of voids. Calcining, of course, is not essential to the broad aspects of this invention and is only required where, for example, template resides in the micropores.

Where the discontinuous assembly of nano-sized molecular sieve is located outside the pores of the meso/macroporous structure, it may be desirable to bond at least a portion of the particles to the surface of the structure. This can be accomplished in a number of ways. For instance, the surface of the structure can be functionalized with hydroxyl groups or other moieties that would be reactive with a zeolitic molecular sieve. For polymeric molecular sieves, the surface may be functionalized with moieties that react, such as addition or condensation, with functional moieties on the polymer. These techniques are well known in the art for other applications.

Similar preparation techniques can be used where it is desired to incorporate at least a portion of the molecular sieve particles in the pores of the meso/macroporous structure. The molecular sieve particles should be of an appropriate size to enter the meso/macropores. A pressure differential may be used to draw barrier particles into the pores or ultrasonication may be used to aid in getting barrier particles into the pores of the meso/macroporous support. The depth of the molecular sieve particles in the pores of the meso/macroporous structure should not be so great as to unduly reduce permeance. Often, any surface deposition of molecular sieve is removed by, e.g., washing.

If desired, zeolitic molecular sieves can be grown in situ in the pores of the meso/macroporous structure to provide a discontinuous membrane. The synthesis may provide discrete particles or islands between other structure such as the meso/macroporous structure or other particles.

An example of using other particles to make discontinuous membranes of zeolitic molecular sieves, involves providing silica, which may have a particle size of between 5 and 20 nanometers, in or on the meso/macroporous structure. The silica, due to the active hydroxyls on the surface, serves as a nucleating site for a zeolite-forming, precursor solution, and layers of zeolite can be grown on and between the silica particles.

Materials other than silica particles can be used as nucleating sites including other molecular sieves or seed crystals of the same zeolite. The surface of the meso/macroporous structure can be functionalized to provide a selective location for zeolite growth. Some zeolites have self nucleating properties and thus may be used in the absence of nucleating sites. Examples of these zeolites are FAU and MFI. In these situations, it may be desired to maintain the precursor solution under zeolite forming conditions for a time sufficient that growth of the zeolite starts prior to contacting the precursor solution with the meso/macroporous structure.

For example, one method to form a barrier layer is to place a zeolitic molecular sieve precursor liquid on a meso/microporous structure. The precursor is permitted to crystallize under hydrothermal crystallization conditions, after which the membrane is washed and heated to remove residual organic material. The molecular sieve material resides primarily in and occludes the pores of the porous substrate.

The molecular sieve may be of any suitable combination of elements to provide the sought pore structure. Aluminum, silicon, boron, gallium, tin, titanium, germanium, phosphorus and oxygen have been used as building blocks for molecular sieves such as silica-alumina molecular sieves, including zeolites; silicalite; AlPO; SAPO; and boro-silicates. The precursor includes the aforementioned elements, usually as oxides or phosphates, together with water and an organic structuring agent which is normally a polar organic compound such as tetrapropyl ammonium hydroxide. Other adjuvants may also be used such as amines, ethers and alcohols. The mass ratio of the polar organic compound to the building block materials is generally in the range of 0.1 to 0.5 and will depend upon the specific building blocks used. In order to prepare thin layers of molecular sieves in the membranes, it is generally preferred that the precursor solution be water rich. For instance, for silica-alumina molecular sieves, the more ratio of water to silica should be at least 20:1 and for aluminophosphate molecular sieves, the mole ratio should be at least 20 moles of water per mole of aluminum.

The crystallization conditions are often in the range of 80° C. to 250° C. at pressures in the range of 100 to 1000, frequently 200 to 500, kPa absolute. The time for the crystallization is limited so as not to form an unduly thick layer of molecular sieve. In general, the crystallization time is less than 50, say, 10 to 40, hours. Preferably the time is sufficient to form crystals but less than that required to form a molecular sieve layer of 200 nanometers, say, 5 to 50 nanometers. The crystallization may be done in an autoclave. In some instances, microwave heating will effect crystallization in a shorter period of time. The membrane is then washed with water and then calcined at 350° to 550° C. to remove any organics.

Especially with some zeolitic molecular sieve materials, making particles less than 100 nanometers is troublesome. Moreover, even with the use of seed crystals, the particle size may be larger than desired. Another embodiment in making a discontinuous barrier membrane is to synthesize the zeolite in open regions between particles (substrate particles) having a major dimension less than 100 nanometers. Accordingly, the major dimension of the microporous barrier can be less than 100 nanometers. The substrate particles serve as a nucleating site for the zeolite formation and thus are selected from materials having capability of nucleating the growth of the zeolite. Examples of such materials are silica, especially silica having a major dimension of between 5 and 50 nanometers and other zeolites having major dimensions less than 100 nanometers. The use of fumed silica as the substrate particle is particularly useful for making an AlPO microporous barrier.

The growth of the zeolite on the substrate particle may occur before or after the substrate particle is used in forming the membrane composite.

Advantageously, the growth of the zeolite on the substrate particles occurs while drawing the synthesis liquor through the composite. This technique helps ensure that the growth occurs not as a layer on top of the particles, but in the interstices between the particles. The pressure drop increases as the zeolite growth occurs, and the pressure drop can be used as an indicator when adequate zeolite formation has occurred.

Polymeric molecular sieves can be synthesized in the meso/macroporous structure. One method for synthesizing a small polymeric molecular sieve is to functionalize nanoparticles and/or the meso/macroporous structure with a group that can react with an oligomer such as through a condensation or addition reaction. For instance, the functional groups may provide a hydroxyl, amino, anhydride, dianhydride, aldehyde, amic acid, carboxyl, amide, nitrile, or olefinic moiety for addition or condensation reaction with a reactive moiety of an oligomer. Suitable oligomers may have molecular weights of 30,000 to 500,000 or more and may be reactive oligomers of polysulfones; poly(styrenes) including styrene-containing copolymers; cellulosic polymers and copolymers; polyamides; polyimides; polyethers; polyurethanes; polyesters; acrylic and methacrylic polymers and copolymers; polysulfides, polyolefins, especially vinyl polymers and copolymers; polyallyls; poly(benzimidazole); polyphosphazines; polyhydrazides; polycarbodiides, and the like.

The synthesis in situ of the molecular sieve, whether it be inorganic or organic, can be under suitable conditions. A preferred technique involves conducting the synthesis while drawing the reactant solution, e.g., the precursor solution or oligomer solution through the meso/macroporous structure. This technique provides the benefit of directing the reactant solution to voids that have not been occluded as well as limits the extent of growth of the molecular sieve as no fresh reactant will be able to enter the reaction site once the molecular sieve has occluded the meso- or macropore.

The molecular sieve on polymer support membranes or polymeric supports themselves may also be pyrolyzed in a vacuum furnace to produce a carbon membrane. For such membranes containing molecular sieves, the pore structure of the carbon support is preferably of sufficient diameter to minimize the resistance to the flow of fluids with the molecular sieve structure doing the separation. The temperature of the pyrolysis will depend upon the nature of the polymer support and will be below a temperature at which the porosity is unduly reduced. Examples of polymeric supports include polyimides, polyacrylonitrile, polycarbonates, polyetherketones, polyethersulfones and polysulfones, and prior to pyrolysis, the supports have pores or openings in the range of 2 to 100, preferably 20 to 50, nanometers.

Continuous membranes may be prepared by any suitable technique. Typically, the thickness of the microporous barrier will be related to the duration of the deposition or growth of the microporous barrier on the meso/macroporous structure. The microporous barrier may be formed by reducing the pore size of an ultrafiltration membrane (effective pore diameters of 1 to 100 nanometers) or a microfiltration membrane (effective pore diameters of 100 to 10,000 nanometers) by, e.g., organic or inorganic coating of the channel either interior of the surface, or preferably, at least partially proximate to the opening of the channel. The deposited material serves to provide a localized reduction of the pores or openings through the support to a size which permits the desired sieving without unduly reducing the diameter of the remaining pore structure in the support. Examples of vapor depositable materials include silanes, paraxylylene, alkylene imines, and alkylene oxides. Another technique for reducing pore size is to deposit a coke layer on the meso/macroporous structure. For instance, a carbonizable gas such as methane, ethane, ethylene or acetylene can be contacted with the structure at sufficiently elevated temperature to cause coking. The preferred porous supports are ultrafiltration membranes having pore sizes of between 1 and 80, preferably between 2 and 50, nanometers.

For zeolitic, continuous membranes, one fabricating technique involves contacting the surface of the meso/macroporous structure with precursor for molecular sieve and growing the molecular sieve for a time sufficient to achieve the sough film thickness. The procedures disclosed above can be used to synthesize the molecular sieve. In some instances, it may be desirable to occlude, e.g., with a wax, the meso/macropores of the support to prevent undue growth of zeolite in those pores. The wax can subsequently be removed.

Various techniques are available to enhance the selectivity of high flux membranes. Numerous techniques exist to cure defects in continuous or discontinuous membranes. As the membranes need not exhibit high $C_6$ Permeate Flow Ratios to be useful for many applications, any technique that increases resistance to flow through the defects will serve to improve membrane performance. For instance, a silica sol overlay coating may be used to occlude interstitial openings between the molecular sieve crystals or remaining large pores in the support regardless of how the membrane is prepared.

Another technique to occlude large pores is to provide on one side of the barrier layer a large, reactive molecule which is not able to permeate the micropores of the barrier and on the other side a cross linking agent. The major defects, and to some extent the minor defects become filled with the large, reactive molecule and are fixed by crosslinking. The unreacted large molecule component can then be removed as well as unreacted crosslinking agent. The large molecule may be an oligomer or large molecule.

For discontinuous membranes, solid may be provided in at least a portion of the voids between particles or islands of microporous barrier and between the microporous barrier and the meso/microporous structure.

One generic technique for enhancing the selectivity of a sieving membrane is to agglomerate adjacent particles of molecular sieve to reduce or substantially eliminate voids between the particles and between the particles and walls of the pore structure in the meso/macroporous structure. Because the particles are nano-sized and the number of adjacent particles can be relatively few, the agglomeration can occur while still retaining desirable Permeant Flow Rates. For polymeric molecular sieves that are thermoplastic, the agglomeration can occur by heating to a temperature where agglomeration occurs but no so high as to lose either its microporous structure or its ability to provide the desired occlusion of the meso- or macropore of the meso/macroporous structure. Agglomeration can also be accomplished by calcining zeolitic molecular sieves. Calcining tends to agglomerate small zeolite particles, especially particles that are neither silated nor otherwise treated to reduce the tendency to agglomerate. The temperature and duration of the calcining will depend upon the nature of the zeolitic molecular sieve. Usually temperatures of between 450° C. and 650° C. are employed over a period of between 2 and 20 hours.

The agglomeration technique may be used with respect to molecular sieve particles that are on the surface of the meso/macroporous structure as well as those within the pores of the structure. Most preferably, agglomeration is used when the molecular sieve particles are located within the meso- or macropores of the meso/macroporous structure such that the major dimension of the agglomerate is less than 200, preferably less than 100, nanometers. The agglomeration may be effected with or without a pressure differential across the membrane. Preferably a pressure differential is used to assist in reducing voids through which fluid can by-pass the molecular sieve.

Another generic technique where the discontinuous assembly of barrier defines voids is to at least partially occlude at least a portion of the voids by a solid material therein. Preferably the solid material is a polymer or inorganic material. The solid material may simply to reside in the void or it may adhere or be bonded to the molecular sieve or meso/macroporous structure. The solid material may be a particle or oligomer that may be preformed and then introduced into the voids or it may be formed in situ.

In one aspect, the solid material provides a "mortar" with the microporous barrier particles. The mortar is typically a suitable polymeric material that can withstand the conditions of the separation. Representative polymers include polysulfones; poly(styrenes) including styrene-containing copolymers; cellulosic polymers and copolymers; polyamides; polyimides; polyethers; polyurethanes; polyesters; acrylic and methacrylic polymers and copolymers; polysulfides, polyolefins, especially vinyl polymers and copolymers; polyallyls; poly(benzimidazole); polyphosphazines; polyhydrazides; polycarbodiides, and the like. Preferred polymers are those having porosity such as PIMs (see WO 2005/012397) and polymers in which porosity has been induced by pore forming agents. These polymers have pores that may be 0.3 or more, preferably at least 1, nanometer in major dimension and hence allow for fluid flow to and from the barrier particles.

It is not necessary that all particles be encased in the mortar. Often the average thickness of the mortar layer is less than 100 nanometers, and is preferably no more than the major dimension of the particles. If too much mortar is used, a mixed membrane structure may result, and flux unduly penalized. Hence, the mass ratio of barrier particles to mortar often is in the range of between 1:2 to 100:1, preferably between 3:1 to 30:1.

The mortar and particles may be admixed, e.g., in a slurry, and then placed in association with the microporous structure, or may be provided after deposition of the particles. The polymer may be formed in situ at the region containing the barrier particles. The barrier particle may be inert to the polymerization or may have active sites to anchor a polymer. For instance, the particle may be functionalized with a reactive group that can bind with the polymer or with monomer undergoing polymerization, say, through a condensation or addition mechanism such as discussed above.

A concern is that the mortar occludes the micropores of the molecular sieve. With highly porous polymer such as the PIMs, the effect of any occlusion can be attenuated. Often, the amount of polymer used for the mortar and its molecular weight and configuration is such that insufficient polymer is present for encapsulating all the molecular sieve particles. Frequently, the mass ratio of polymer to molecular sieve is between 0.01:1 and 0.3:1. The weight average molecular weight of the polymer is sometimes in the range of 20,000 to 500,000, preferably, between 30,000 and 300,000.

The mortar may be other than polymeric. For example, where the molecular sieve is a zeolite, a silicon tetraalkoxide can react with the zeolite and can through hydrolysis form a silica framework or mass between the molecular sieve particles. Usually a dilute aqueous solution of silicon tetraalkoxide is used, e.g., containing between 0.5 and 25 mass percent silicon tetraalkoxide, to assure distribution. The functionalization of the zeolite with silicon tetraalkoxide also is useful as a cross-linking site with organic polymer, especially those containing functional groups such as hydroxyl, amino, anhydride, dianhydride, aldehyde or amic acid groups that can form covalent bonds with organosilicon alkoxide. Also, the same or different zeolite may be grown between the zeolite particles and the zeolite particles and the meso/macroporous structure using the techniques described above.

Yet another approach to reducing bypass is to use two or more sized particles in forming the barrier-containing layer. If, for example, the microporous barrier particles are generally spherical with a nominal major dimension of 60 nanometers, the regions between the particles can be sizable and enable bypass. Incorporating configurationally compatible particles in these regions can hinder fluid flow and thus result in a greater portion of the fluid being directed to the barrier particles for the selective separation. The configuration of the barrier particles will depend upon the type of barrier particle used. A microporous zeolitic molecular sieve particle having a major dimension of less than 100 nanometers will likely have a defined configuration due to its crystalline structure. Some zeolites tend to have a platelet-type configuration whereas others, such as AlPO-14, have a rod-like structure. Similarly, polymeric, ceramic, glass and carbon molecular sieve particles may have configurations that are not readily changed. Hence, the configuration of the open regions between particles can vary widely.

Sometimes, the configurationally compatible particles are selected to achieve at least partial occlusion of the region. Thus, for spherical barrier particles rod shaped or much smaller configurationally compatible particles may be desired. The configurationally compatible particles may be of any suitable composition given the size and conditions of operation. The particles may be polymeric, including oligomeric; carbon; and inorganic such as fumed silica, zeolite, alumina, and the like.

DETAILED DESCRIPTION OF THE DRAWING

With reference to FIG. 1, a linear paraffin-containing feedstock is supplied to an isomerization unit via line 102. Hydrogen is provided via line 104. The combined stream passes to isomerization reactor 106. The effluent from isomerization reactor 106 is directed via line 108 to stabilizer column 110. In stabilizer column 110, lights are removed as an overhead via line 112. The lights may be used for any suitable purpose including for fuel value. The bottoms from stabilizer column 110 are passed through line 114 to deisohexanizer 116. A side stream from deisohexanizer is recycled via line 118 to isomerization reactor 106. A bottoms stream from deisohexanizer 116 is removed via line 120. The overhead from deisohexanizer 116 is passed via line 122. The bottoms stream is passed via line 120 to the retentate side of membrane separator 124. A stream having a lesser concentration of normal hexane is removed from separator 124 via line 126, and the permeate fraction which contains normal hexane is recycled via line 128 to isomerization reactor 106.

The invention claimed is:

1. A process for isomerizing a feedstock comprising paraffins having between 5 and 7 carbon atoms wherein at least about 15 mass-percent of the feedstock is linear paraffin to provide an isomerate comprising:
   a. isomerizing a feedstock under isomerization conditions including the presence of isomerization catalyst to provide an isomerization effluent containing linear paraffins including normal hexane but in a concentration less than that in the feedstock,
   b. distilling at least a portion of the isomerization effluent to provide a lower boiling fraction containing dimethylbutanes, a higher boiling fraction containing normal hexane and methylpentanes, and a bottoms stream containing normal hexane and heavies, wherein the higher boiling fraction contains less than about 75 mass percent of the normal hexane subjected to distillation in this step b, and the bottoms stream contains at least about 25 mass percent of the normal hexane subjected to distillation in this step b, c. contacting at least a portion of the bottoms stream from step b with a retentate-side of a selectively permeable sieving membrane under conditions including sufficient membrane surface area and pressure differential across the membrane to provide a retentate fraction of the bottoms stream that has a reduced concentration of normal hexane, and to provide across the membrane at a permeate-side, a permeate fraction having an increased concentration of normal hexane, said permeate fraction containing at least about 50 mass-percent of the normal hexane contained in the bottoms stream contacted with the membrane, wherein the sieving membrane has a $C_6$ Permeate Flow Index of at least about 0.01 and a $C_6$ Permeate Flow Ratio of at least about 1.25:1; and d. passing at least a portion of the permeate fraction of step c to step a.

2. The process of claim 1 wherein at least a portion of the higher boiling fraction is passed to step a.

3. The process of claim 1 wherein the permeate fraction contains at least 75 mass percent of the normal hexane contained in the bottoms stream contacted with the membrane.

4. The process of claim 1 wherein the permeate fraction contains at least 90 mass percent of the normal hexane contained in the bottoms stream contacted with the membrane.

5. The process of claim 1 wherein the octane rating of the lower boiling fraction from step b is at least 88 RONC.

6. The process of claim 1 wherein the sieving membrane has an average pore diameter of 5.0 to 7.0 Å.

7. The process of claim 1 wherein the sieving membrane has an average pore diameter of 4.5 to 5.4 Å.

* * * * *